United States Patent
Nam et al.

(10) Patent No.: US 10,835,470 B2
(45) Date of Patent: Nov. 17, 2020

(54) COSMETICS COMPOSITION CONTAINING GINSENOSIDE AS ACTIVE INGREDIENT

(71) Applicant: AMOREPACIFIC CORPORATION, Seoul (KR)

(72) Inventors: Gi Baeg Nam, Yongin-si (KR); Dong Hyun Kim, Yongin-si (KR); Yong Deog Hong, Yongin-si (KR); Cheng Yi Zhang, Yongin-si (KR); Jun Seong Park, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 15/772,272

(22) PCT Filed: Oct. 26, 2016

(86) PCT No.: PCT/KR2016/012083
§ 371 (c)(1),
(2) Date: Apr. 30, 2018

(87) PCT Pub. No.: WO2017/074022
PCT Pub. Date: May 4, 2017

(65) Prior Publication Data
US 2018/0318198 A1    Nov. 8, 2018

(30) Foreign Application Priority Data
Oct. 30, 2015    (KR) .................. 10-2015-0152448

(51) Int. Cl.
| | |
|---|---|
| *A61K 8/63* | (2006.01) |
| *A61Q 19/02* | (2006.01) |
| *A61Q 19/00* | (2006.01) |
| *A61K 8/60* | (2006.01) |
| *A61Q 17/00* | (2006.01) |
| *A61Q 19/08* | (2006.01) |

(52) U.S. Cl.
CPC .............. *A61K 8/63* (2013.01); *A61K 8/60* (2013.01); *A61Q 17/005* (2013.01); *A61Q 19/00* (2013.01); *A61Q 19/007* (2013.01); *A61Q 19/02* (2013.01); *A61Q 19/08* (2013.01)

(58) Field of Classification Search
None
See application file for complete search history.

(56) References Cited

U.S. PATENT DOCUMENTS

2009/0169623 A1*    7/2009    Sene ................ A61K 8/97
                                                    424/474
2011/0318397 A1    12/2011    Lee et al.

FOREIGN PATENT DOCUMENTS

| CN | 105267049 A | 1/2016 |
|---|---|---|
| KR | 10-2014-0004897 | 1/2014 |
| KR | 10-2014-0022618 | 2/2014 |
| KR | 10-2014-0026818 | 3/2014 |
| KR | 10-2015-0074774 | 7/2015 |
| KR | 10-2015-0078868 | 7/2015 |
| WO | WO 2015/029134 A1 | 3/2015 |
| WO | WO 2016/035182 A1 | 3/2016 |

OTHER PUBLICATIONS

Song et al, "Panaz ginseng has anti-infective activity against opportunistic pathogen *Pseudomonas aeruginosa* inhibiting quorum sensing, a bacterial communication process critical for establishing infection", *Phytomedicine*, Nov. 2010; 17(13); pp. 1040-0146, NIH Public Access Author Manuscript.
TW Office Action and English translation thereof dated May 18, 2020 in TW Application No. 105134718.
Lee et al, "Fermenting Red Ginseng Enhances Its Safety and Efficacy as a Novel Skin Care Anti-Aging Ingredient: In Vitro and Animal Study", Journal of Medicinal Food, vol. 15, No. 11, Nov. 2012, pp. 1015-1023.
Dou et al, "The Inhibitory Effects of Gensenosides on Protein Tyrosine Kinase Activated by Hypoxia/Reoxygenation in Cultured Human Umbilical Vein endothelial Cells", Planta Medica, vol. 67, No. 1, Jan. 1, 2001, pp. 19-23.

(Continued)

*Primary Examiner* — David J Blanchard
*Assistant Examiner* — Sarah J Chickos
(74) *Attorney, Agent, or Firm* — Nixon & Vanderhye P.C.

(57) ABSTRACT

The present invention relates to a cosmetic composition comprising a compound represented by Formula 1 below as an active ingredient.

[Formula 1]

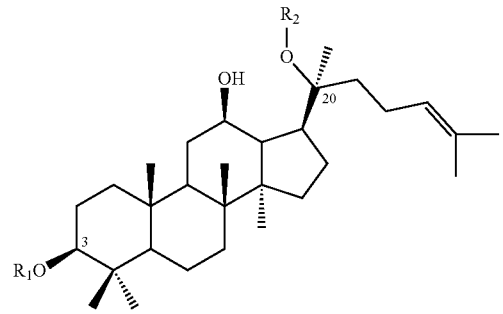

in the above Formula 1, $R_1$ is -glc(2-1)glc, $R_2$ is -glc, or $R_1$ is -glc, $R_2$ is -glc(6-1)ara(pyr).

8 Claims, No Drawings

(56) References Cited

OTHER PUBLICATIONS

Straseski et al, "Oxygen deprivation inhibits basal keratinocyte proliferation in a model of human skin and induces regio-specific changes in the distribution of epidermal adherens junction proteins, aquaporin-3, and glycogen", Wound Repair and Regeneration, vol. 17, No. 4, Jul. 1, 2009, pp. 606-616.
EP Communication and Extended Search Report dated Jul. 16, 2019 in EP Application 16860205.0.
EP Communication dated Mar. 23, 2020 in EP Application 16860205.0.

* cited by examiner

COSMETICS COMPOSITION CONTAINING GINSENOSIDE AS ACTIVE INGREDIENT

PRIORITY CLAIM

This application is the U.S. national phase of International Application No. PCT/KR2016/012083 filed 26 Oct. 2016, which designated the U.S. and claims priority to KR Patent Application No. 10-2015-0152448 filed 30 Oct. 2015, the entire contents of each of which are hereby incorporated by reference.

TECHNICAL FIELD

The present invention relates to a cosmetic composition comprising ginsenoside as an active ingredient.

This application claims the benefit of priority from Korean Patent Application No. 10-2015-0152448 filed on Oct. 30, 2015, the full disclosure of which is incorporated herein by reference.

BACKGROUND ART

*Panax ginseng* consists of flower (fruit) and stem of the aboveground part and roots (main roots, fine roots) of the underground part, among which the underground part of *ginseng* is used medicinally for a long time in the oriental region. Saponin, a main component of medicinal action of *ginseng*, is also called ginsenoside, and it has the meaning of glycoside isolated from *ginseng*. Ginsenoside of *panax ginseng* includes protopanaxatriol-type ginsenosides (PPT; Rg1, Re, Rf, Rh1, Rg2) and protopanaxadiol-type ginsenosides (PPD; Rb1, Rc, Rb2, Rb3, Rd, Rg3, Rh2, Compound-K). As the pharmacological action and clinical effect of such ginsenoside, central nervous system depression and excitement action, protein and nucleic acid biosynthesis-promoting action, hematopoietic action, arteriosclerosis prevention, hypoglycemic effect, anti-fatigue and anti-stress action and the like are known.

Ginsenoside includes ingredients that can be acquired by isolating *ginseng* extracts with an equipment such as chromatography, but each amount resulting from specific ingredients is small.

The method of converting such ginsenosides using enzymes has recently been developed, and its efficacies have been actively studied by ginsenoside whose structure has been converted. However, the structure of ginsenoside has diversified, and thus the efficacy due to each ginsenoside structure has not yet been concretely identified.

DETAILED DESCRIPTION OF THE INVENTION

Technical Problem

An object of the present invention is to provide a cosmetic composition which has excellent anti-oxidative power, excellent skin aging prevention effect, excellent skin moisturizing effect, excellent skin whitening effect, anti-inflammatory effect, effect of improving skin trouble such as acne and atopy, sebum control effect, pore shrinkage effect, and effect of improving complexion through improvement of blood circulation.

Technical Solution

The name of the compound referred to in the present specification means a compound corresponding to INCI (International Nomenclature Cosmetic Ingredient) Name which is listed in International Cosmetic Ingredient Dictionary (ICID) published by Cosmetic, Toiletry and Fragrance Association (CTFA), unless otherwise specified. If the relevant name does not exist in the INCI Name, it means a compound according to the IUPAC nomenclature established by the International Union of Pure and Applied Chemistry (IUPAC). Unless a compound according to the IUPAC nomenclature is present, it means a compound corresponding to the name of a compound commonly used in the technical field to which the present invention pertains.

The present invention provides a cosmetic composition comprising a compound represented by Formula 1 below as an active ingredient.

[Formula 1]

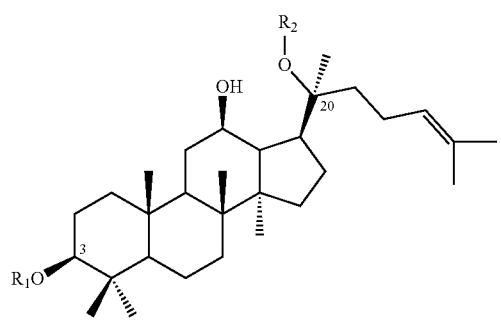

in the above Formula 1, $R_1$ is -glc(2-1)glc, $R_2$ is -glc, or $R_1$ is -glc, $R_2$ is -glc(6-1)ara(pyr).

Advantageous Effects

The cosmetic composition according to the present invention has excellent antioxidant power, excellent skin aging prevention effect, excellent skin moisturizing effect, excellent skin whitening effect, anti-inflammatory effect, effect of improving skin trouble such as acne and atopy, sebum control effect, pore shrinkage effect, and effect of improving complexion through improvement of blood circulation.

DETAILED DESCRIPTION OF THE EMBODIMENTS

Hereinafter, the cosmetic composition according to the present invention will be described in detail.

The cosmetic composition according to the present invention includes a compound represented by Formula 1 below as an active ingredient.

[Formula 1]

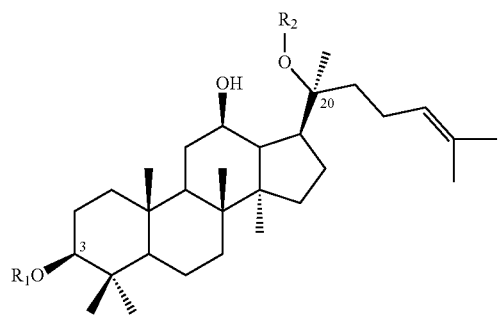

in the above Formula 1, $R_1$ is -glc(2-1)glc, $R_2$ is -glc, or $R_1$ is -glc, $R_2$ is -glc(6-1)ara(pyr).

In one embodiment of the present invention, the compound is ginsenoside Rd wherein, in Formula 1, $R_1$ is -glc(2-1)glc and $R_2$ is -glc.

In one embodiment of the present invention, the compound is a compound O wherein, in Formula 1, $R_1$ is -glc and $R_2$ is -glc(6-1)ara(pyr).

As used herein, the glc means β-D-glucopyranosyl group, the ara(pyr) means L-arabinopyranosyl group, the ara(fur) means L-arabinofuranosyl group, and the rha means α-L-rhamnopyranosyl group.

As used herein, the ginsenoside means glycoside of saponin isolated from *ginseng*. In the technical field to which the present invention pertains, the structure of ginsenoside is specifically named ginsenoside Rx. In ginsenoside Rx, "R" means radix or root and "x" is named in the order of o, a, b, c, d, e, f, g, h, etc., from the lower side to the upper side according to the moving distance (Rf value) appearing on TLC (Thin Layer Chromatography).

The ginsenoside compound and the structure thereof according to the above-described ginsenoside nomenclature are shown in Table 1 below, and all the structures thereof are represented by the Formula 1 and differ only in the substituents of R1 and R2 in the Formula.

TABLE 1

| Name of ginsenoside compound | Substituents of Formula 1 | |
| --- | --- | --- |
| | $R_1$ | $R_2$ |
| Ginsenoside Rb1 | -glc(2-1)glc | -glc-glc |
| Ginsenoside Rb2 | -glc(2-1)glc | -glc-ara(pyr) |
| Ginsenoside Rc | -glc(2-1)glc | -glc-ara(fur) |
| Ginsenoside Rd | -glc(2-1)glc | -glc |
| Compound O | -glc | -glc(6-1)ara(pyr) |

In one embodiment of the present invention, the ginsenoside can be isolated from the extract of *ginseng*, and the *ginseng* extract is extracted from roots, stems, leaves or fruits of *ginseng*, preferably from roots or leaves of *ginseng*. However, the *ginseng* extract in the present invention is not limited to the extraction site thereof.

In one embodiment of the present invention, the *ginseng* extract can be obtained by filtering a whole or a part of dried *ginseng* with water, a lower alcohol having the number of carbon atoms 1 to 4 or a mixed solvent thereof, preferably methanol, and concentrating the resultant under reduced pressure, but the present invention is not limited by the extraction method.

In one embodiment of the present invention, preferably, organic solvents such as n-hexane, ethyl acetate, n-butanol or the like are sequentially added to a *ginseng* extract, and then subjected to purification and fractionation, and thereby the ginsenoside can be isolated using chromatography such as silica gel column chromatography, LH-20 column chromatography, thin layer chromatography (TLC), high performance liquid chromatography or the like. However, the present invention is not limited by the separation method.

In the present specification, *Panax ginseng* means a perennial grass plant of the family Aralia.

In one embodiment of the present invention, the content of ginsenoside is 0.001% to 10% by weight relative to the total weight of the composition.

The cosmetic composition according to the present invention is excellent in antioxidant effect to inhibit the formation and action of active oxygen. Therefore, in one embodiment of the present invention, the cosmetic composition is for antioxidation.

The cosmetic composition according to the present invention is excellent in antioxidant effect and thus excellent in the effect of preventing skin aging due to antioxidation. Therefore, in one embodiment of the present invention, the cosmetic composition is for anti-aging.

The cosmetic composition according to the present invention is excellent in skin whitening effect that inhibits the production and action of tyrosinase and melanin. Therefore, in one embodiment of the present invention, the cosmetic composition is for skin whitening.

The cosmetic composition according to the present invention has an excellent ability to increase skin moisture content. Therefore, in one embodiment of the present invention, the cosmetic composition is for skin moisturizing.

The cosmetic composition according to the present invention has an excellent ability to improve skin elasticity and thus an excellent wrinkle improving effect. Therefore, in one embodiment of the present invention, the cosmetic composition is for improving skin wrinkles.

In one embodiment of the present invention, the cosmetic composition is for improving acne, and the cosmetic composition is excellent in antimicrobial effect, particularly, antimicrobial effect against acne-causing bacteria, and provides an anti-inflammatory effect, and thus may be for antimicrobial use, The cosmetic composition according to the present invention suppresses sebum secretion when applied to a skin and has an excellent effect of controlling sebum secretion, has excellent effect of controlling sebum secretion and suppressing the occurrence of dandruff when applied the scalp. Thus, the cosmetic composition according to the present invention is for sebum control.

The cosmetic composition according to the present invention can smoothly supply nutrients to the skin by expanding capillary vessels when applied to the skin, and it has an excellent effect of improving the complexion of skin and skin tone by suppressing skin aging. Therefore, the cosmetic composition according to the present invention is for improving a complexion.

The present invention provides antioxidant use in the production of a cosmetic composition containing the compound represented by the Formula 1 as an active ingredient.

The present invention provides anti-aging use in the production of a cosmetic composition containing the compound represented by the Formula 1 as an active ingredient.

The present invention provides a skin whitening use in the production of a cosmetic composition containing the compound represented by the Formula 1 as an active ingredient.

The present invention provides a skin moisturizing use in the production of a cosmetic composition containing the compound represented by the Formula 1 as an active ingredient.

The present invention provides a use for improving skin wrinkles in the production of a cosmetic composition containing the compound represented by the Formula 1 as an active ingredient.

The present invention provides a use for improving acne in the production of a cosmetic composition containing the compound represented by the Formula 1 as an active component.

The present invention provides antimicrobial use in the production of a cosmetic composition containing the compound represented by the Formula 1 as an active ingredient.

The present invention provides an anti-inflammatory use in the production of a cosmetic composition containing the compound represented by the Formula 1 as an active ingredient.

The present invention provides a use for improving a complexion in the production of a cosmetic composition containing the compound represented by the Formula 1 as an active ingredient.

The present invention provides a use for regulating sebum in the production of a cosmetic composition containing the compound represented by the Formula 1 as an active ingredient.

The present invention provides an anti-oxidative method comprising a step of applying a cosmetic composition containing the compound represented by the Formula 1 as an active ingredient to a skin.

The present invention provides an anti-aging method comprising a step of applying a cosmetic composition containing the compound represented by the Formula 1 as an active ingredient to a skin.

The present invention provides a skin whitening method comprising a step of applying a cosmetic composition containing the compound represented by the Formula 1 as an active ingredient to a skin.

The present invention provides a skin moisturizing method comprising a step of applying a cosmetic composition containing the compound represented by the Formula 1 as an active ingredient to a skin.

The present invention provides a method for improving skin wrinkles comprising a step of applying a cosmetic composition containing the compound represented by the Formula 1 as an active ingredient to a skin.

The present invention provides a method for improving acne comprising a step of applying a cosmetic composition containing the compound represented by the Formula 1 as an active ingredient to a skin.

The present invention provides an antimicrobial method comprising a step of applying a cosmetic composition containing the compound represented by the Formula 1 as an active ingredient to a skin.

The present invention provides an anti-inflammatory method comprising a step of applying a cosmetic composition containing the compound represented by the Formula 1 as an active ingredient to a skin.

The present invention provides a method for improving a complexion comprising a step of applying a cosmetic composition containing the compound represented by the Formula 1 as an active ingredient to a skin.

The present invention provides a method for regulating sebum comprising a step of applying a cosmetic composition containing the compound represented by the Formula 1 as an active ingredient to a skin.

The composition of the present invention can be formulated as a skin external preparation composition, particularly a cosmetic composition. The composition can be formulated containing a cosmetically or dermatologically acceptable medium or base. In addition, the compositions of the present invention can be provided in all dosage forms adapted for topical application. For example, it can be provided in a dosage form including, for example, a solution, an emulsion obtained by dispersing an oil phase in an aqueous phase, an emulsion obtained by dispersing an aqueous phase in an oil phase, a suspension, a solid, a gel, a powder, a paste, a foam or an aerosol composition. Compositions of such dosage forms can be prepared by conventional methods known in the art.

In addition, the composition according to the present invention may include, in addition to the above-mentioned substances, other components that can preferably impart a synergistic effect to the main effect, within the range that does not damage the main effect. Furthermore, the composition according to the present invention may further include a humectant, an emollient agent, an ultraviolet absorber, a preservative, a disinfectant, an antioxidant, a pH adjuster, organic and inorganic pigments, a flavoring agent, a cold-sensing agent or an antiperspirant. The blending amount of the above ingredients can be easily selected by those skilled in the art within the range that does not impair the object and effect of the present invention, and the blending amount thereof may be 0.001% to 10% by weight, specifically 0.001% to 1% by weight, relative to the total weight of the composition.

Hereinafter, the present invention will be described in more detail with reference to examples. However, these examples are provided herein for illustrative purposes only and are not intended to limit the scope of the present invention in any way.

<Reference Example 1> Preparation of Ginsenoside Rd

Ginsenoside Rd for testing the efficacy of the composition of the present invention was purchased from a pure product GINSENOSIDE (product name: Ginsenoside Rd) manufactured by Ambo Institute and used in the test.

<Reference Example 2> Preparation of Compound O

Compound O for testing the efficacy of the composition of the present invention was purchased and used as a pure product GINSENOSIDE (product name: Compound O) manufactured by Ambo Laboratories.

<Test Example 1> Inhibitory Effects on Generation of Reactive Oxygen Species (ROS)

$5 \times 10^4$ keratinocytes (cell line: HaCaT; obtained from: ATCC) was placed in each well of a 24-well plate and allowed to adhere for 24 hours. After 16 hours, ginsenoside Rd was treated with 1%. At this time, for comparison, the control group did not treat ginsenoside Rd. After 2 hours, the culture solution was removed, and 100 µl of phosphate buffer saline (PBS) was added to each well. The keratinocytes were irradiated with ultraviolet rays of 30 mJ/cm$^2$ using an ultraviolet B (UVB) lamp (Model: F15T8, UV B 15 W, Sankyo Denki, Japan), and then PBS was taken out and 200 µl of keratinocyte culture solution was added to each well. Herein, ginsenoside Rd was again treated and the amount of reactive oxygen species increased by ultraviolet stimulation was determined for each fixed period of time. The amount of ROS was determined by referring to Tan's method for measuring the fluorescence of DCF-DA (dichlorofluorescin diacetate) oxidized by ROS (Tan et al., 1998, J. Cell Biol. Vol. 141, pp 1423-1432). The ratio of the control group treated only with vehicle to the ROS was calculated and the results are shown in Table 2 below. The ginsenoside Rd was replaced with Compound O, and the test was carried out in the same process. The results are also shown in Table 2 below.

TABLE 2

| Test substance | Elapsed time after irradiation of UVB 30 mJ/cm² | | |
|---|---|---|---|
| | 0 hr | 2 hr | 3 hr |
| Vehicle | 100 | 244 | 287 |
| UVB + Vehicle | 100 | 325 | 381 |
| UVB + Ginsenoside Rd | 100 | 251 | 286 |
| UVB + Compound O | 100 | 251 | 286 |

From the results in Table 2, it can be seen that ginsenoside Rd and Compound O according to the present invention effectively suppress the production of ROS, which is known to cause skin cell damage by ultraviolet rays, and the anti-oxidative effect is extremely excellent at the level that the amount of ROS after ultraviolet stimulation suppresses the production of ROS at almost the same level as the case where ROS is not irradiated. Therefore, the cosmetic composition according to the present invention suppresses oxidation and prevents aging, thereby preventing enlargement of the pores. Moreover, it was confirmed that skin trouble can be improved by protecting the occurrence of skin irritation.

<Test Example 2> Tyrosinase Inhibitory Effects

The tyrosinase enzyme was extracted from mushrooms and obtained from Sigma (SIGMA). First, tyrosine as a substrate was dissolved in distilled water to prepare 0.3 mg/ml of a solution. The solution was placed by 1.0 ml in a test tube, and then 1.0 ml of potassium phosphate buffer solution (concentration 0.1 mol, PH 6.8) and 0.7 ml of distilled water were added to prepare a reaction solution.

0.2 ml of the test substance was placed in the reaction solution, and then the mixture was allowed to react in a thermostatic chamber at 37° C. for 10 minutes. At this time, as a negative control group (no addition), that obtained by adding 0.2 ml of only solvent in place of each test substance was prepared. As a positive control group, ascorbic acid was used. 2500 unit/ml of tyrosinase solution was added by 0.1 ml to the reaction solution, and the mixture was reacted again in a thermostatic chamber at 37° C. for 10 minutes. The test tube containing this reaction solution was placed in ice water and quenched to stop the reaction. Absorbance at a wavelength of 475 nm was measured with a photoelectron spectrometer. The results are shown in Table 3 below. Each tyrosinase inhibitory effect was calculated by Mathematical Equation 1 below. The tests were conducted on ginsenoside Rd and compound O, respectively.

Tyrosinase inhibition rate (%)=100−[{(Reaction absorbance of test substance)/(Reaction absorbance of negative control group)} ×100]  [Mathematical Equation 1]

TABLE 3

| Test substance | Tyrosinase inhibition rate (%) |
|---|---|
| Negative control group (no addition) | 0 |
| Ascorbic acid | 56 |
| Ginsenoside Rd | 68 |
| Compound O | 76 |

From the results in Table 3, it can be seen that ginsenoside Rd and compound O have excellent tyrosinase inhibitory effect. Further, it can be confirmed that compositions containing ginsenoside Rd or compound O can provide extremely excellent skin whitening effect.

<Test Example 3> Inhibitory Effects on Melanin Production Using B16/F10 Melanoma Cells The B16/F10 melanoma used in this test example is a cell line derived from a mouse and is a cancer cell caused by malignant alteration of a cell secreting a black pigment called melanin. The extent to which and melanin production was decreased by treating the test substance during artificial cultivation of this cell was compared and evaluated. The B16/F10 melanoma used in this test example was purchased from the Korean Cell Line Bank (KCLB No: 8008) and used.

Measurement of melanin biosynthesis inhibitory effect of B16/F10 melanoma was carried out as follows. B16/F10 melanoma was dispensed in a 6-well plate (5×10⁵/well) and cultured in DMEM (Dulbecco's Modified Eagle's Medium) containing 10% FBS (fetal bovine serum) for about 24 hours at 37° C. in a 5% $CO_2$ incubator (MCO-20 AIC, Sanyo). The test substance was added to a new DMEM medium not containing FBS and allowed to stand for 72 hours. The test substances used here are as shown in Table 4 below. Trypsin-EDTA was treated and centrifuged to separate the cells. Then, melanin was dissolved at 95° C. with 1N NaOH containing DMSO. Absorbance was measured at 405 nm using an ELISA reader (DIbiotech, Korea). The cells to which the test substance was not added were used as a control group. In comparison with the melanin content in the control group, the degree of inhibition of melanin production of each test substance was measured. Kojic acid was used as a positive control group. Melanin production inhibition rate was calculated according to Mathematical Equation 2 below, and the results are shown in Table 4.

Melanin production inhibition rate (%)=100−[{(Absorbance of test substance)/(Absorbance of control group)}×100]  [Mathematical Equation 2]

TABLE 4

| Test substance | Melanin production inhibition rate (%) |
|---|---|
| Control group (no addition) | 0 |
| Kojic acid | 49 |
| Ginsenoside Rd | 67 |
| Compound O | 71 |

From the results in Table 4, it can be confirmed that ginsenoside Rd or Compound O has an increased rate of inhibition of melanin production, and that a composition containing ginsenoside Rd or Compound O can provide extremely excellent skin whitening effect.

<Reference Example 3> Preparation of Drug Formulations 1 and 2 and Comparative Formulation 1

Nutritive creams were produced by an usual manner according to the composition in Table 5 below (unit: wt %).

TABLE 5

| Blending ingredient | Formulation 1 | Formulation 2 | Comparative Formulation 1 |
|---|---|---|---|
| Purified water | To 100 | To 100 | To 100 |
| Ginsenoside Rd | 0.5 | — | — |
| Compound O | — | 0.5 | — |
| Vegetable hardened oil | 1.50 | 1.50 | 1.50 |
| Stearic acid | 0.60 | 0.60 | 0.60 |
| Glycerol stearate | 1.00 | 1.00 | 1.00 |
| Stearyl alcohol | 2.00 | 2.00 | 2.00 |
| Polyglyceryl-10 pentastearate & behenyl alcohol & sodium stearoyl lactylate | 1.00 | 1.00 | 1.00 |
| Arachidyl behenyl alcohol & arachidyl glucoside | 1.00 | 1.00 | 1.00 |
| Cetylaryl Alcohol and Cetearyl Glucoside | 2.00 | 2.00 | 2.00 |
| PEG-100 Stearate & Glycerololate & Propylene Glycol | 1.50 | 1.50 | 1.50 |
| Caprylic/capric triglyceride | 11.00 | 11.00 | 11.00 |
| Cyclomethicone | 6.00 | 6.00 | 6.00 |
| Preservative, fragrance | Adequate amount | Adequate amount | Adequate amount |
| Triethanol amine | 0.1 | 0.1 | 0.1 |

<Test Example 4> Measurement of Effects of Increasing Skin Moisturizing Power

In order to measure the effect on the increase in skin moisturizing power of the composition of the present invention, the above-mentioned Formulations 1 and 2 and Comparative Formulation 1 were used and evaluated as described below.

30 male and female adults in their 40s to 50s classified as dry skin were divided into three groups each consisting of 10 with respect to the 3 groups of Formulations 1 and 2 and Comparative Formulation 1, and nutritive creams were applied to the face twice daily for 4 weeks. Skin moisture content was measured with a skin moisture content measuring device (Corneometer CM 825, C+K Electronic Co., Germany) under constant temperature and humidity conditions (24° C. and relative humidity 40%) before the start of the application, at the time of the elapse of 1 week, 2 weeks and 4 weeks after the application, and at the time of the elapse of 2 weeks after the stop of the application (elapse of 6 weeks in total). The results are shown in Table 6 below. The results in Table 6 express the increase rate (%) in measured values after treatment for a certain period of time based on the value of the skin moisture content measuring device measured immediately before the start of the test.

TABLE 6

| Test group | Moisture increase rate (%) | | | |
|---|---|---|---|---|
| | Elapse of 1 week | Elapse of 2 weeks | Elapse of 4 weeks | Elapse of 6 weeks |
| Formulation 1 | 29 | 31 | 31 | 33 |
| Formulation 2 | 29 | 32 | 34 | 32 |
| Comparative Formulation 1 | 27 | 30 | 28 | 17 |

Looking at the results in Table 6, it can be confirmed that, when Comparative Formulation 1 is applied, it shows a moisture increase rate of about 30% or less until 4 weeks from the application, but after the application is stopped, skin moisture content sharply decreases, and that, when Formulation 1 or Formulation 2 containing ginsenoside Rd or Compound O is applied, it shows a skin moisture increase rate of 30% or more even after the application is stopped. This shows that the composition of the present invention is excellent in skin moisturizing effect.

<Test Example 5> Measurement of Antibacterial Activity

Antibacterial experiments were conducted to evaluate the antibacterial activity of ginsenoside Rd and Compound O. Specific experimental methods are as follows.

The strains of Staphylococcus aureus, Escherichia coli and Pseudomonas aeruginosa used in the experiment were cultured in Trypticase Soy Broth, and the strains of Candida albicans, Aspergillus niger were cultured in Sabouraud Dextrose Broth medium. A diluted solution in which the culture solution is diluted 1/100 (Candida albicans strain 1/10) in each culture medium was used as a test strain solution. A spore suspension of Aspergillus niger ($2\times10^8$ cfu/ml) was used as a test strain solution.

A solution prepared by adding 0.15 ml of the test strain solution to 15 ml of each medium and thoroughly mixing the same was used as a diluted solution.

96 Deep well plate was placed by 16 μl ginsenoside Rd 10 ppm to 1 row and placed by 184 μl a diluted solution. The diluted solution was placed by 100 μl in the rest of the wells. The mixed solution of 1 row was thoroughly mixed and 100 μl was taken and placed in 2 row and thoroughly mixed. 100 μl was taken again and placed in 3 row. A two-fold dilution was carried out in this manner.

Staphylococcus aureus, Escherichia coli and Pseudomonas aeruginosa were cultured in a thermostatic chamber at 32° C., and Candida albicans and Aspergillus niger were cultured in a thermostatic chamber at 25° C. After 48 hours, the growth of strains was checked by the degree of suspension and microscope, and the Minimum Inhibitory Concentration (MIC) value was determined. The results are shown in Table 7 below. The ginsenoside Rd was replaced with Compound O, and the test was carried out in the same process. The results are also shown in Table 7 below.

TABLE 7

| Test group | Minimum Inhibitory Concentration (MIC), unit % | | | | |
|---|---|---|---|---|---|
| | Pseudomonas aeruginosa | Staphylococcus aureus | Escherichia coli | Candida albicans | Aspergillus niger |
| Ginsenoside Rd | 0.25 | 0.07 | 0.191 | >4 | >3 |
| Compound O | 0.11 | 0.4 | 0.162 | >3 | >1 |

<Test Example 6> Measurement of Sebum Reduction Effect

In order to investigate the sebum secretion suppressing effect of the Formulations 1 and 2 and Comparative Formulation 1, evaluation was carried out as follows. Thirty male and female subjects who felt that sebum secretion was high were selected, and nutritive creams of Formulations 1 and 2 and Comparative Formulation 1 were applied daily for 4 weeks to the designated site. The effect of sebum reduction was determined by measuring the average sebum reduction rate (%) after 2 weeks and 4 weeks using a sebum amount measuring instrument (Sebumeter SM 810, C+K Electronic Co., Germany). The results are shown in Table 8 below.

TABLE 8

| Test substance | Sebum reduction rate (%) | |
|---|---|---|
| | After elapse of 2 weeks | After elapse of 4 weeks |
| Formulation 1 | 33 | 41 |
| Formulation 2 | 35 | 43 |
| Comparative Formulation 1 | 5 | 5 |

From the results in Table 8, it can be seen that Formulation 1 containing ginsenoside Rd according to the present invention as an active ingredient can effectively suppress excessive secretion of sebum than Comparative Formulation 1 which does not contain the same. Further, it can be seen that Formulation 2 containing the Compound O according to the present invention as an active ingredient can effectively suppress excessive secretion of sebum as compared with Comparative Formulation 1 which does not contain the same.

Hereinafter, the formulation examples of the composition according to the present invention will be described, but the pharmaceutical composition and the cosmetic composition can be applied to various dosage forms. This is not intended to limit the present invention, but merely for the purpose of illustration.

[Formulation Example 1] Cosmetic Skin

Cosmetic skin is prepared according to a conventional method with the composition described in Table 9 below.

TABLE 9

| | Content (wt %) |
|---|---|
| Ginsenoside Rd and/or Compound O | 1.0 |
| Glycerin | 3.0 |
| Butylene glycol | 2.0 |

TABLE 9-continued

| | Content (wt %) |
|---|---|
| Propylene glycol | 2.0 |
| Carboxyvinyl polymer | 0.1 |
| PEG 12 nonylphenyl ether | 0.2 |
| Polysorvate 80 | 0.4 |
| Ethanol | 10.0 |
| Triethanol amine | 0.1 |
| Preservative, pigment, flavoring agent | Adequate amount |
| Purified water | Residual amount |

[Formulation Example 2] Nutritive Cream

Nutritive cream was prepared according to a conventional method with the composition shown in Table 10 below.

TABLE 10

| | Content (wt %) |
|---|---|
| Ginsenoside Rd and/or Compound O | 1.0 |
| Polysorvate 60 | 1.5 |
| Sorbitan sesquioleate | 0.5 |
| PEG 60 hardened castor oil | 2.0 |
| Liquid paraffin | 10.0 |
| Squalane | 5.0 |
| Caprylic/capric triglyceride | 5.0 |
| Glycerin | 5.0 |
| Butylene glycol | 3.0 |
| Propylene glycol | 3.0 |
| Triethanol amine | 0.2 |
| Preservative, pigment, flavoring agent | Adequate amount |
| Purified water | Residual amount |

[Formulation Example 3] Massage Cream

Massage cream was prepared according to a conventional method with the composition shown in Table 11 below.

TABLE 11

| | Content (wt %) |
|---|---|
| Ginsenoside Rd and/or Compound O | 0.5 |
| Bees wax | 10.0 |
| Polysorvate 60 | 1.5 |
| PEG 60 hardened castor oil | 2.0 |
| Sorbitan sesquioleate | 0.8 |
| Liquid paraffin | 40.0 |
| Squalane | 5.0 |
| Caprylic/capric triglyceride | 4.0 |
| Glycerin | 5.0 |
| Butylene glycol | 3.0 |

TABLE 11-continued

|  | Content (wt %) |
| --- | --- |
| Propylene glycol | 3.0 |
| Triethanol amine | 0.2 |
| Preservative, pigment, flavoring agent | Adequate amount |
| Purified water | Residual amount |

[Formulation Example 4] Pack

Pack was prepared according to a conventional method with the composition shown in Table 12 below.

TABLE 12

|  | Content (wt %) |
| --- | --- |
| Ginsenoside Rd and/or Compound O | 0.5 |
| Polyvinyl alcohol | 13.0 |
| Sodium carboxymethyl cellulose | 0.2 |
| Glycerin | 5.0 |
| Allantoin | 0.1 |
| Ethanol | 6.0 |
| PEG 12 nonylphenyl ether | 0.3 |
| Polysorvate 60 | 0.3 |
| Preservative, pigment, flavoring agent | Adequate amount |
| Purified water | Residual amount |

[Formulation Example 5] Gel

Gel was prepared according to a conventional method with the composition shown in Table 13 below.

TABLE 13

|  | Content (wt %) |
| --- | --- |
| Ginsenoside Rd and/or Compound O | 0.25 |
| Ethylene diamine sodium acetate | 0.05 |
| Glycerin | 5.0 |
| Carboxy vinyl polymer | 0.3 |
| Ethanol | 5.0 |
| PEG 60 hardened castor oil | 0.5 |
| Triethanol amine | 0.3 |
| Preservative, pigment, flavoring agent | Adequate amount |
| Purified water | Residual amoumt |

[Formulation Example 6] Ointment

Ointment was prepared according to a conventional method with the composition shown in Table 14 below.

TABLE 14

|  | Content (wt %) |
| --- | --- |
| Ginsenoside Rd and/or Compound O | 0.5 |
| Glycerin | 8.0 |
| Butylene glycol | 4.0 |
| Liquid paraffin | 15.0 |

TABLE 14-continued

|  | Content (wt %) |
| --- | --- |
| Beta glucan | 7.0 |
| Carbomer | 0.1 |
| Caprylic/capric triglyceride | 3.0 |
| Squalane | 1.0 |
| Cetearyl glucoside | 1.5 |
| Sorbitan stearate | 0.4 |
| Cetearyl Alcohol | 1.0 |
| Bees wax | 4.0 |
| Preservative, pigment, flavoring agent | Adequate amount |
| Purified water | Residual amount |

Although specific parts of the present invention have been described in detail, it will be apparent to those skilled in the art that these specific techniques are merely a preferred embodiment and that the scope of the present invention is not limited thereto. Therefore, the substantial scope of the present invention will be defined by the accompanying claims and their equivalents.

The invention claimed is:

1. A cosmetic composition comprising an effective amount of a combined mixture of Ginsenoside Rd and Compound O represented by Formula 1 below:

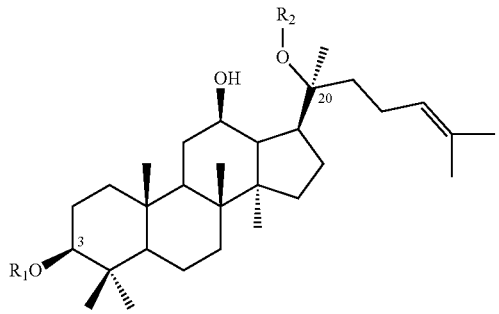

[Formula 1]

wherein Ginsenoside Rd is represented by Formula 1 in which $R_1$ is -glc(2-1)glc and $R_2$ is -glc, wherein Compound O is represented by Formula 1 in which $R_1$ is -glc and $R_2$ is -glc(6-1)ara(pyr), and wherein the effective amount of the combined mixture is 0.25 to 1.0% by weight relative to the total weight of composition.

2. The cosmetic composition of claim 1 wherein the cosmetic composition is for antioxidation.

3. The cosmetic composition of claim 1 wherein the cosmetic composition is for anti-aging.

4. The cosmetic composition of claim 1 wherein the cosmetic composition is for skin whitening.

5. The cosmetic composition of claim 1 the cosmetic composition is for skin moisturizing.

6. The cosmetic composition of claim 1 the cosmetic composition is for improving skin wrinkles.

7. The cosmetic composition of claim 1 wherein the cosmetic composition is for antimicrobial use.

8. The cosmetic composition of claim 1 the cosmetic composition is for sebum control.

\* \* \* \* \*